United States Patent
Rostene et al.

(10) Patent No.: US 9,439,981 B2
(45) Date of Patent: Sep. 13, 2016

(54) METHOD FOR INCREASING THE INTRAOCULAR PRESSURE IN AN ANIMAL

(75) Inventors: William Rostene, Paris (FR); Christophe Baudouin, Paris (FR); David Godefroy, Paris (FR); Alexandre Denoyer, Paris (FR)

(73) Assignees: INSTITUT NATIONAL DE LA SANTE ET DE LA RECHERCHE MEDICALE (INSERM), Paris (FR); CENTRE NATIONAL DE LA RECHERCHE SCIENTIFIQUE, Paris (FR); UNIVERSITE VERSAILLES SAINT-QUENTIN-EN-YVELINES, Versailles (FR)

( * ) Notice: Subject to any disclaimer, the term of this patent is extended or adjusted under 35 U.S.C. 154(b) by 45 days.

(21) Appl. No.: 14/235,097

(22) PCT Filed: Jul. 27, 2012

(86) PCT No.: PCT/EP2012/064840
§ 371 (c)(1),
(2), (4) Date: Jan. 27, 2014

(87) PCT Pub. No.: WO2013/017551
PCT Pub. Date: Feb. 7, 2013

(65) Prior Publication Data
US 2014/0178308 A1 Jun. 26, 2014

(30) Foreign Application Priority Data
Jul. 29, 2011 (EP) .................................... 11305993

(51) Int. Cl.
*A61K 31/14* (2006.01)
*A61K 49/00* (2006.01)
*A01K 67/027* (2006.01)

(52) U.S. Cl.
CPC ......... *A61K 49/0008* (2013.01); *A01K 67/027* (2013.01); *A61K 31/14* (2013.01)

(58) Field of Classification Search
CPC .................................................... A61K 31/14
See application file for complete search history.

(56) References Cited

U.S. PATENT DOCUMENTS 4,039,662 A * 8/1977 Hecht .................. A61K 9/0048
514/54

FOREIGN PATENT DOCUMENTS

WO 2009/109900 A1 9/2009

OTHER PUBLICATIONS

Morrison et al., "A Rat Model of Chronic Pressure-Induced Optic Nerve Damage", Exp Eye Res, 1997, pp. 85-96, vol. 64.
Guo et al., "Retinal Ganglion Cell Apoptosis in Glaucoma Is Related to Intraocular Pressure and IOP-Induced Effects on Extracellular Matrix", IOVS, Jan. 1, 2005, vol. 46, No. 1, pp. 175-182.
Elena et al., "Ocular pharmacokinetics of two preservatives: Benzalkonium chloride or benzoxonium chloride, after installation in the pigmented rabbit", Experimental Eye Research, Sep. 1, 1992, p. 4, vol. 55, Academic Press Ltd., London, GB.
Britton et al., "Intraocular irritation evaluation of benzalkonium chloride in rabbits", Database EMBASE, 1976, Elsevier, Web.

* cited by examiner

*Primary Examiner* — Zohreh Fay
(74) *Attorney, Agent, or Firm* — Whitham, Curtis & Cook, P.C.

(57) ABSTRACT

The present invention concerns a method for inducing an increase in the intraocular pressure in an animal, said method comprising ocular administration of a solution comprising benzalkonium chloride (BAK). The present invention further relates to an animal having ocular hypertension, said animal being obtained by the method according to the invention. Said animal provides a convenient animal model for better understanding of the patho-physiological mechanisms involved in ocular hypertension and glaucoma. The present invention also relates to the use of said animal for screening a compound for therapeutic use against ocular hypertension or glaucoma, and/or for assessing potential side-effects of treatment of ocular hypertension and glaucoma.

4 Claims, 5 Drawing Sheets

METHOD FOR INCREASING THE INTRAOCULAR PRESSURE IN AN ANIMAL

The present invention concerns a method for inducing an increase in the intraocular pressure in an animal, said method comprising ocular administration of a solution comprising benzalkonium chloride (BAK). The present invention further relates to an animal having ocular hypertension, said animal being obtained by the method according to the invention. Said animal provides a convenient animal model for better understanding of the patho-physiological mechanisms involved in ocular hypertension and glaucoma. The present invention also relates to the use of said animal for screening a compound for therapeutic use against ocular hypertension or glaucoma, and/or for assessing potential side-effects of treatment of ocular hypertension and glaucoma.

BACKGROUND OF THE INVENTION

Glaucoma is an eye disorder in which the optic nerve suffers damage, permanently impacting vision in the affected eye and progressing to complete blindness if untreated. It is often associated with increased pressure of the aqueous humour in the eye. The term 'ocular hypertension' is used for cases having constantly raised intra-ocular pressure with or without associated optic nerve damage.

Glaucoma is the second leading cause of blindness worldwide. However, if the condition is detected early enough it is possible to arrest the development or slow down the progression with medical and surgical means.

The major risk factor for most glaucomas and focus of treatment is increased intraocular pressure. Intraocular pressure is a function of production of liquid aqueous humor by the ciliary processes of the eye and its drainage through the trabecular meshwork. Aqueous humor flows from the ciliary processes into the posterior chamber. It then flows through the pupil of the iris into the anterior chamber. From here the trabecular meshwork drains aqueous humor via Schlemm's canal into scleral plexuses and general blood circulation. Glaucoma may be due to reduced flow through the trabecular meshwork (open angle glaucoma) or to complete closure of the iridocorneal angle resulting in the inability of the aqueous fluid to flow from the posterior to the anterior chamber and then out of the trabecular network (angle closure glaucoma).

Medical treatment of glaucoma includes medication and surgery. In particular, intraocular pressure can be lowered with medication, usually eye drops. Both laser surgeries and conventional surgeries are performed to treat glaucoma, which include canaloplasty, laser surgery, trabeculectomy, glaucoma drainage implants.

The development of animal models of glaucoma by intra-ocular hypertonia is still a major issue in experimental research in this disease. The development of reliable models is necessary to understand the physio-pathology of the disease as well as evaluating the therapeutic potential of new molecules.

PRIOR ART

The anterior segment is the front third of the eye that includes the cornea, iris, ciliary body, and lens. Within the anterior segment are two fluid-filled spaces: the anterior chamber between the posterior surface of the cornea and the iris, and the posterior chamber between the iris and the front face of the vitreous. Aqueous humor fills these spaces within the anterior segment and provides nutrients to the surrounding structures.

Ocular hypertension occurs when the intra-ocular pressure increases as a consequence of over-production of liquid aqueous humor in the eye, or as a consequence of reduction of its drainage through the trabecular meshwork. Aqueous humour is secreted into the posterior chamber by the ciliary body. It normally flows through the narrow cleft between the front of the lens and the back of the iris, to escape through the pupil into the anterior chamber, and then to drain out of the eye via the trabecular meshwork. From here, it drains into Schlemm's canal via the episcleral veins and eventually into the veins of the orbit. Ocular hypertension models known in the art are based on physical modification of the eye structures, such as e.g. ligature or cauterization.

The DBA/2j mice model relies on trabecular obstruction due to iris pigment dispersion. This model of obstructive glaucoma displays only a low and transient ocular hypertension and is associated with high variability and lack of reproducibility (Chang et al. Nat Genet 1999; John et al, IOVS 1998; Reichstein et al, Exp eye Res 2007; Inman et al, IOVS 2006).

Another model, the trabecular photocoagulation model, has been obtained in rodents and monkeys by trabecular obstruction by photodestruction. Photodestruction, performed using a laser, is used to induce an obstruction of the trabecular vessels. Consequently, drainage of aqueous humor through the trabecular meshwork is prevented and intra-ocular pressure increased. However, this model has been effective only in monkeys, which are difficult and restrictive to work with due to legal restrictions, ethical requirements and the complex facilities needed to perform experiments in primates. Moreover, studying trabecular pathophysiology with this model is rendered impossible due to direct physical destruction (Ghasterland et al. IOVS 1974; Radisu et al. ARch Ophth 1984; Zhang et al, exp eye res 2009; Levkovitch-Verbin et al, IOVS 2002; Ueda et al, Jpn J Ophthalmol 1998).

A third model is a trabecular obstruction model obtained in rats and monkeys by the use of beads. To obtain this model, beads are injected in the eyes of the animal, near the trabeculum. Consequently, the trabecular meshwork is obstructed by the beads, leading to intra-ocular pressure increase. Effectiveness has been reported for acute ocular hypertension. However, this model displays high variability, and morphological study of the trabeculum is altered by the presence of the beads (Weber et al. J NeuroScience methods 2001; Urcola et al, Exp eye Res 2006).

Another model relies on episcleral vein occlusion by ligature or cauterization in rats. Aqueous humour present in the anterior chamber normally drains out of the eye via the trabecular meshwork and then the episcleral veins. Occlusion of the latter prevents aqueous humour drainage and lead to intra-ocular pressure increase. Some authors have reported obtaining durable ocular hypertension using this method. Morphology of the anterior segment appears to be preserved in this model and comparable to that of primary open-angle galucome (POAG) (Garcia-Valenzuela et al, Exp eye Res 1995; Park et al, J Ocul Pharmacol Ther 2008; Yu et al, Exp eye Res 2008; Nissirios et al, IOVS 2008; Danias et al, exp eye Res 2006). However, such a model is surgically not easy to set up, and requires many animals to be checked for long-term ocular hypertension.

A final model is based on chemical modifications of the eye structures by episcleral injection of hypertonic saline in rats. This injection results in episcleral trabecular obstruction and destruction. However, this model is associated with significant morphological alterations, such as e.g. enlargement of the anterior chamber (AC) and destruction of the ciliary. Moreover, the resulting modifications are only temporary and do not provide a long-term model of glaucoma (Morrison et al, exp eye Res 1997; Guo et al, IOVS 2005).

Thus validated models known in the art require complex and poorly reproducible surgical procedures, and show variable efficacy rates depending on the experimenter. Moreover, these models are not always relevant to the pathology of glaucoma. The development of a simple and robust model would be of major interest for fundamental research on intra-ocular hypertonia and glaucoma and for industrial validation of current and future treatments against this disease.

DESCRIPTION OF THE INVENTION

The inventors have shown that injection of benzalkonium chloride (BAK) in animal eyes increases the intra-ocular pressure, reduces outflow facility and increases trabecular cell apoptosis (see Example 2). BAK is a chemical commonly used as a stabilizer or a disinfectant in ocular medicines. However, the inventors have surprisingly shown that, when used at higher concentrations than usual, BAK induces trabeculum apoptosis and obstruction leading to intra-ocular pressure increase and thus to ocular hypertonia.

Increased intra-ocular pressure reduced outflow facility and increased trabecular cell apoptosis are the main physiopathological characteristics of glaucoma. Thus, the increase in the intraocular pressure obtained in the method according to the invention may be used as a model of glaucoma.

In one aspect, the invention relates to a method for inducing an increase in the intraocular pressure in an animal, said method comprising ocular administration of a solution comprising benzalkonium chloride (BAK).

Preferably, the method according to the invention is not a method of treatment, in particular a method of treatment of the human or animal body by surgery or therapy. Optionally, the method further comprises measuring the intraocular pressure in said animal.

The solution for intraocular administration may comprise various concentrations of BAK.

Ocular administration of the solution comprising BAK may be done by various methods such as, for instance, injection. Injection of the solution comprising BAK may be performed in various regions of the animal eyes.

The method for inducing an increase in the intraocular pressure in an animal according to the invention may comprise single or multiple administrations of the solution comprising BAK. When multiple administrations are done, the time lapse between two successive administrations of the solution comprising BAK may vary.

The present invention further relates to an animal having ocular hypertension, said animal being obtained by the method according to the invention.

An animal obtained by the method of the invention will preferably display increased intra-ocular pressure, reduced outflow facility and increased trabecular cell apoptosis. Thus, in a specific embodiment, said animal is for use as a model of glaucoma. The invention further relates to the use of an animal having ocular hypertension as a model of glaucoma, said animal being obtained by the method of the invention. Methods of screening are also provided.

In a specific embodiment, the animal of the invention is for use for screening a compound for therapeutic use against ocular hypertension or glaucoma. Alternatively, another embodiment concerns the use of an animal having ocular hypertension for screening a compound for therapeutic use against ocular hypertension or glaucoma, said animal being obtained by the method of the invention.

Alternatively, the animal of the invention may also be for use for studying the mechanisms of ocular hypertension, i.e. the aqueous humour turn-over and pathological processes involved in trabecular outflow resistance, as well as of glaucoma and processes linking ocular hypertension and trabecular pathology with retinal ganglion cell loss and visual impairments. Another embodiment concerns the use of an animal having ocular hypertension for studying the mechanisms of ocular hypertension or glaucoma, said animal being obtained by the method of the invention.

The animal obtained by the method of the invention may be of any species. It may for instance be a rodent or a primate. Preferably, the animal obtained by the method of the invention is not a human. Typically, the animal obtained by the method of the invention may be a rat or a mouse.

DEFINITIONS

Methods

As used herein, the term benzalkonium chloride refers to the compound also known as alkyldimethylbenzylammonium chloride or ADBAC. Benzalkonium chloride is a mixture of alkylbenzyldimethylammonium chlorides of various even-numbered alkyl chain lengths, of general formula $[C_6H_5—CH_2—N^+(CH_3)_2—R]Cl^-$, R representing $C_8$ to $C_{18}$ "alkyl" radicals. It is typically known in the art under the CAS No. 8001-54-5.

Benzalkonium chloride is a nitrogenous cationic surfaceacting agent belonging to the quaternary ammonium group. Its composition depends on the manufacturing process, including the composition of the starting tertiary amine chosen. It is may be obtained by the reaction of benzyl chloride (alpha-chlorotoluene) in a mixture of dimethylalkylamines. Alternatively, it may be obtained by the action of methyl chloride on (N-alkyl-N-methyl) benzylamine in a suitable solvent medium.

Benzalkonium chloride is mainly used in the pharmaceutical and cosmetic industry and has three main categories of use: as a biocide, a cationic surfactant and phase transfer agent in the chemical industry. The most commonly used industrial products known under this name contain compounds with $C_{12}$ to $C_{18}$ "alkyl" chains with a majority of $C_{12}$ and $C_{14}$. The term benzalkonium chloride refers herein to any type of benzalkonium chloride preparation.

As used herein, the term intra-ocular pressure means the fluid pressure inside the eye. The intra-ocular pressure is a function of the production of liquid aqueous humor by the ciliary processes of the eye and its drainage through the trabecular meshwork. A modification of the intra-ocular pressure may be measured in the animals' eyes by methods well-known by the skilled person using a handheld tonometer. Typically, ocular administration of BAK may increase the intra-ocular pressure by at least 1.5-fold, at least 2-fold, by at least 3-fold or by at least 4-fold.

As used herein, the term ocular hypertension refers to any situation in which the pressure inside the eye, called intraocular pressure, is higher than normal. It may or may not be associated with the presence of optic nerve damage or visual field loss. For instance, current consensus in ophthalmology defines normal intra-ocular pressure as ranging between 10 mmHg and 21 mmHg in humans, which is also accepted in rodents. The term "ocular hypertension" depicts no particular time frame during which the elevated pressure has been measured.

The solution for intraocular administration may comprise various concentrations of BAK. These concentrations may range between a lower limit and an upper limit. In particular, the lower limit may be of 0.01%, 0.02%, 0.03%, 0.04%, 0.05%, 0.06%, 0.07%, 0.08%, 0.09% or 0.1%, and the upper limit may be of 0.3%, 0.4%, 0.5%, 0.6%, 0.7%, 0.8%, 0.9% or 1%. Typically, the solution may comprise a concentration of BAK ranging between 0.01% and 0.5%, and preferably between 0.05% and 0.5%.

According to a specific embodiment, the ocular administration of a solution comprising BAK for inducing an increase in the intraocular pressure in an animal is done by injection, preferably performed under local or general anaesthesia. Said ocular administration of a solution comprising BAK may for instance be performed using a needle connected to a syringe filled with a solution comprising BAK. The injection may be done in various regions of the eye, such as the subconjunctival region, the anterior chamber, or the posterior chamber. BAK exposure could also be performed by ocular administration of topical solution comprising BAK. In a specific embodiment, the injection of the solution comprising BAK is performed in the subconjunctival region of the animal eyes. As used herein, the expression subconjunctival region refers to the anterior segment of the eye. The solution comprising BAK may for instance be injected underneath the conjunctiva so that it can then pass through the sclera and into the eye by simple diffusion. Alternatively, the solution comprising BAK may be injected underneath the conjunctiva and the underlying Tenon's capsule in the more posterior portion of the eye.

The inventors have observed that a first injection of BAK had no effect on intra-ocular pressure. However, they have interestingly shown that the intra-ocular pressure significantly rose and remained significantly elevated after a second injection (see FIG. 1).

Thus, in some embodiments, the method for inducing an increase in the intraocular pressure in an animal according to the invention comprises multiple administrations of the solution comprising BAK. Said method may for instance comprise two administrations, three administrations or four or more administrations of the solution comprising BAK.

The time lapse between two successive administrations of the solution comprising BAK may vary. For instance, the time lapse between two successive administrations of the solution comprising BAK may be of three days, five days, seven days, or nine days.

Animals and Their Uses

The present invention further relates to an animal having ocular hypertension, said animal being obtained by the method according to the invention.

Animals obtained by the method of the invention can be easily distinguished from prior art glaucoma models. Indeed, contrary to prior art animals, animals obtained by the method of the invention do not display any physical characteristics such as e.g. pigmental dispersion, trabeculum destruction, vein ligature or cauterization, as they have not have surgery of any type. Neither do they display trabeculum obstruction due to the presence of a foreign body. Morphologically, animals obtained by the method of the invention only display increased trabecular cell apoptosis, and increased intra-ocular pressure, reduced outflow facility are permanent in these animals.

The animal of the invention can be used as a model of glaucoma. Such a model may for instance be of major interest for industrial validation of current and future treatments against this disease. In one embodiment, therefore, the invention provides a method of screening a compound for therapeutic use in the treatment of ocular hypertension or glaucoma, using the animal of the invention. The invention also concerns the use of said animal for assessing potential side-effects of treatment of ocular hypertension and glaucoma. Said treatment may include, for example, administration of therapeutic compounds that act on ocular hypertension or glaucoma symptoms, as described below.

The compound to be screened for therapeutic use against ocular hypertension or glaucoma may be used for preventing or treating ocular hypertension or glaucoma. Such compound may be any kind of compound that may act on ocular hypertension or glaucoma symptoms. It may for instance decrease secretion of aqueous humor (such as e.g. beta-blockers eyedrops, carbonic anhydrase inhibitors, or alpha2 adrenergic agonist eyedrops), or increase the elimination of aqueous humor (such as e.g. adrenal derivatives, parasympathetic miotic eyedrops, or prostaglandins analogues). The compound to be screened for therapeutic use against ocular hypertension or glaucoma should preferably display a low toxicity.

The screening may for instance include the steps of administering a compound to be screened to at least one eye of an animal of the invention, waiting for a certain period of time, optionally repeating the administration, measuring the intra-ocular pressure or the outflow facility or the level of trabecular cell apoptosis, and selecting the compound if the intra-ocular pressure is higher than a predetermined threshold, or the outflow facility is lower than a predetermined threshold, or the level of trabecular cell apoptosis is higher than a predetermined threshold.

Alternatively, the animal of the invention may also be for use for studying the mechanism of ocular hypertension or glaucoma. Another embodiment concerns the use of an animal having ocular hypertension for studying the mechanism of ocular hypertension or glaucoma, said animal being obtained by the method of the invention. For instance, such an animal can be useful for understanding the physiopathology or the molecular mechanism involved in any eye disease and in particular in ocular hypertension or glaucoma.

The animal obtained by the method of the invention may be of any species. It may for instance be a rodent or a primate. Preferably, the animal obtained by the method of the invention is not a human. In a specific embodiment, the animal obtained by the method of the invention is a rodent. Typically, the animal obtained by the method of the invention may be a rat or a mouse. The animal may be a genetically modified animal, such as a 'knockout' animal in which the function or expression of a gene has been reduced or eliminated.

EXAMPLES

Example 1

Materials and Methods

Animals and Intra-Ocular Pressure Monitoring

Figure 1:
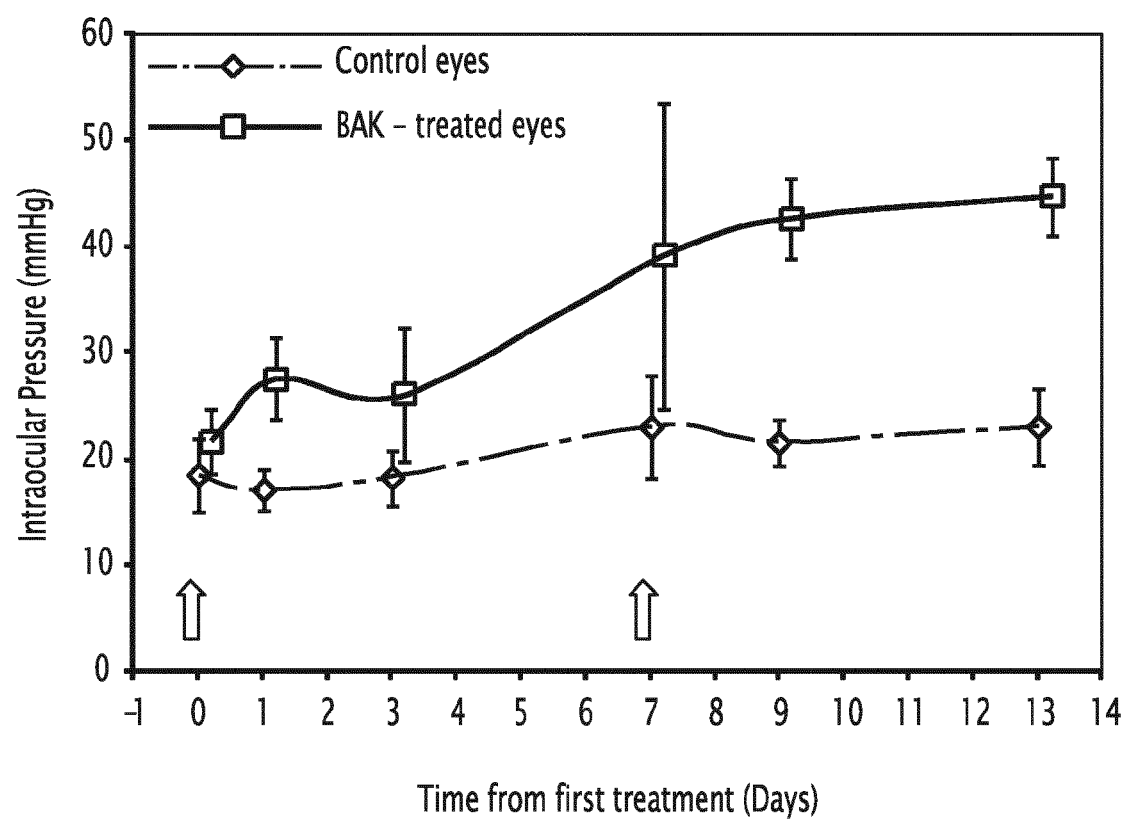
FIG. 1 shows the intra-ocular pressure as a function of the time. Six male 8-week-old Long-Evans rats weighing 300-350 g were used. At D0, first subconjunctival injection of 0.1% BAK (100 µL) was performed in the right eye whereas the left eye received 0.9% NaCl vehicle only as control. A second injection was performed seven days after following the same protocol. Animals were daily monitored for intra-ocular pressure using a handheld tonometer, without sedation. Significant difference between BAK-injected eyes and control eyes was found at D9 and D14 ($P<0.01$).

Six male 8-week-old Long-Evans rats weighing 300-350 g were used. Animals were kept in pathogen-free conditions with food and water available ad libitum and housed in a 12-h light/12-h dark cycle. Ocular integrity was checked using the slit lamp biomicroscope. At D0, first subconjunctival injection of 0.1% BAK (100 µL) was performed in the right eye whereas the left eye received PBS only as control. A second injection was performed seven days after following the same protocol. Animals were daily monitored for intraocular pressure using a handheld tonometer (TonoLab, Medtronics, Jacksonville, Fla., USA) without sedation. All experiments were conducted in accordance with the Association for Research in Vision and Ophthalmology for the Use of Animals in Ophthalmic research.

In Vivo Outflow Facility Measurement

Six days after the second injection of BAK, trabecular outflow facility was measured in vivo under general anaesthesia (intraperitoneal injection of ketamine 75 mg/kg and xylazine 10 mg/kg). Briefly, the eyes were anteriorly canulated with a 30-G needle connected by tubing to a 1 mL syringe filled with PBS and loaded into a microdialysis infusion pump (World Precision instruments). Intraocular pressure was measured after a 10-min stabilization period for three different infusion flow rates (0.1, 0.2, and 0.3 µL/min). Aqueous humor outflow facility (µL/min/mmHg) was calculated as the reciprocal of the slope of the respective ocular pressure/flow rate curves.

Ex Vivo Trabecular Cell Apoptosis

At the end of the experiments, animals were euthanized and the eyes were immediately conditioned for TUNEL labelling. Eyes were fixed in 4% paraformaldehyde, embedded in an optimal cutting-temperature compound (OCT, Tissue-Tek, Miles Inc, Bayer Diagnostic, Püteaux, France) and cut into 15-µm cryosections. A terminal deoxynucleotidyl transferase-mediated dUTP nick-end labelling (TUNEL) assay (Roche Diagnostics, Meylan, France) was performed to detect apoptosis in rat ocular tissues following the manufacturer's instructions. Specimens were mounted in aqueous mounting medium with DAPI to be further analyzed using light epifluorescence microscopy.

Dose-Dependent Effects of Subconjunctival Injections of BAK on Intraocular Pressure Dose-dependent effects of subconjunctival injections of BAK on intraocular pressure were studied in order to determine the minimal concentration required to induce significant ocular hypertension, and to evaluate whether subconjunctival injections of BAK could induce toxic side-effects to the anterior eye.

A series of 3 subconjunctival injections with 0.01% BAK (n=3), 0.05% BAK (n=3), 0.1%, BAK (n=6) or the vehicle (n=4) was performed (0.15 mL, each 48 h during 6 days) in the right eye of animals. Intraocular pressure was measured using a handled tonometer every two days from D0 to D28. Intraocular pressure is expressed as the difference between the treated eye (right) and the left control eye.

In Vivo Assessment of BAK Injection Toxicity to the Ocular Surface

In vivo confocal microscopy (IVCM) using the Heidelberg Retina Tomograph II/Rostock Cornea Module (Heidelberg Engineering GmbH, Heidelberg, Germany) laser-scanning was carried out to assess putative damage to the ocular surface. Images size was 400 per 400 hundred pixels with a lateral resolution of 1 micrometer and an axial resolution of 2 micrometers. IVCM scores were used to evaluate ocular surface toxicity profiles in the 4 groups in different histological regions (superficial epithelium, basal epithelium, anterior stroma, limb and conjunctival stroma).

Example 2

Results

Subconjunctival Injection of BAK Increases the Intra-Ocular Pressure

First injection of 0.1% BAK induced a slight increase in intra-ocular pressure at D7. Interestingly, the increase in intra-ocular pressure became significant after a second administration of 0.1% BAK, as compared to control eyes receiving the vehicle only. Such significant ocular hypertension remained significant until the end of the experiments (FIG. 1).

Subconjunctival Injection of BAK Reduces Outflow Facility

Figure 2:
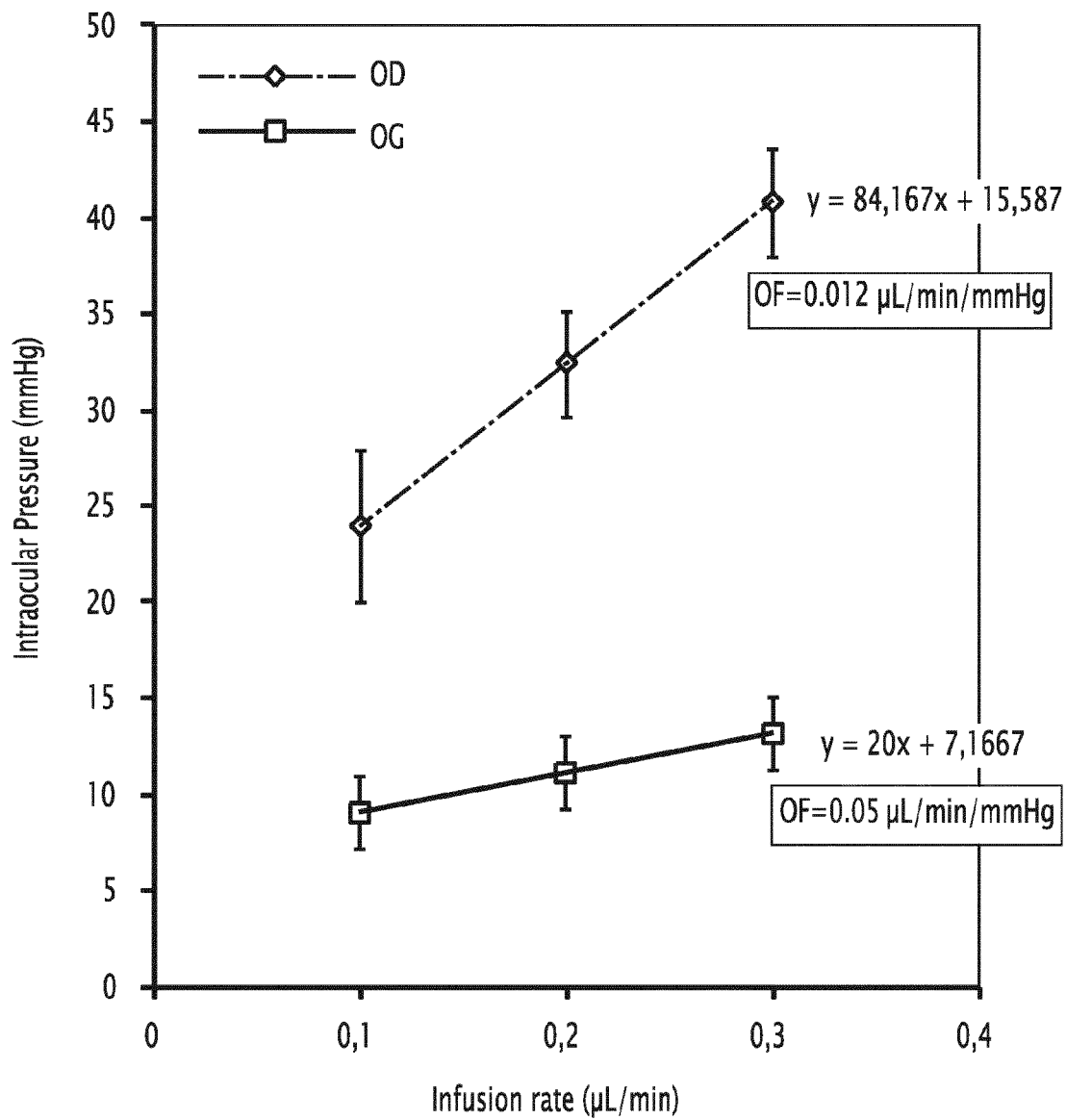
FIG. 2 shows the intra-ocular pressure as a function of the infusion rate. Six days after the second injection of BAK, trabecular outflow facility was measured in vivo under general anaesthesia. The eyes were anteriorly canulated with a 30-G needle connected by tubing to a 1 mL syringe filled with PBS and loaded into a microdialysis infusion pump. Intraocular pressure was measured after a 10-min stabilization period for three different infusion flow rates (0.1, 0.2, and 0.3 µL/min). Aqueous humor outflow facility was calculated as the reciprocal of the slope of the respective ocular pressure/flow rate curves. Outflow facility (OF) was decreased in BAK-injected eyes as compared to vehicle-injected control eyes.
Figure 3:
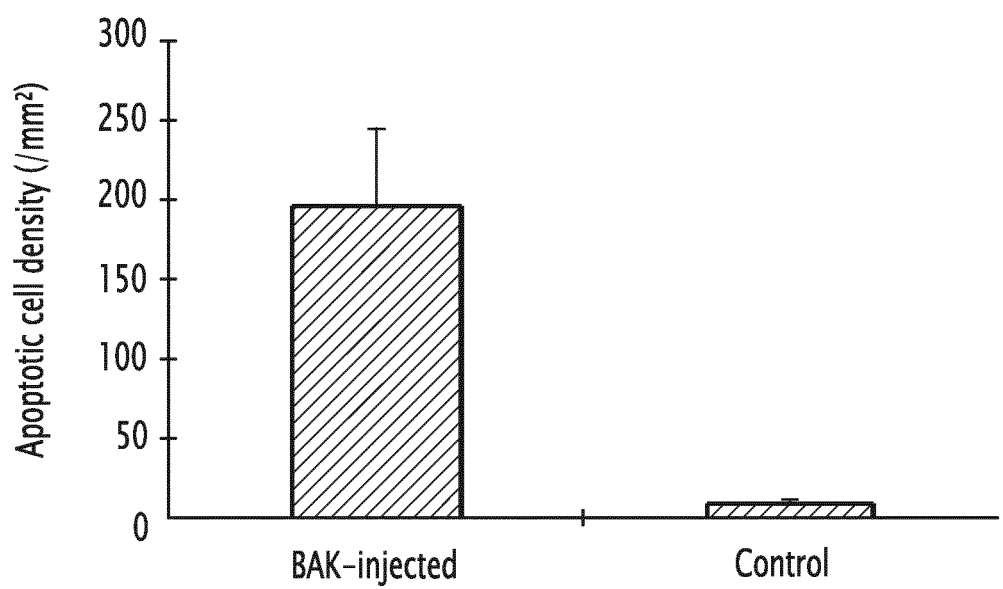
FIG. 3 shows the percentage of trabecular apoptotic cells in BAK-injected eyes compared to controls as assessed by TUNEL labelling. Significant difference was found between BAK-injected eyes and control eyes (P<0.01).

Important increase in intra-ocular pressure with infusion rate revealed a low trabecular outflow facility in BAK-injected eyes compared to control eyes, further confirming that BAK-induced ocular hypertension resulted from an impaired trabecular function (FIG. 2).

Subconjunctival Injection of BAK Increases Trabecular Cell Apoptosis

Trabecular density of apoptotic cells was increased in BAK-injected eyes compared to controls as assessed by TUNEL labelling.

Figure 4:
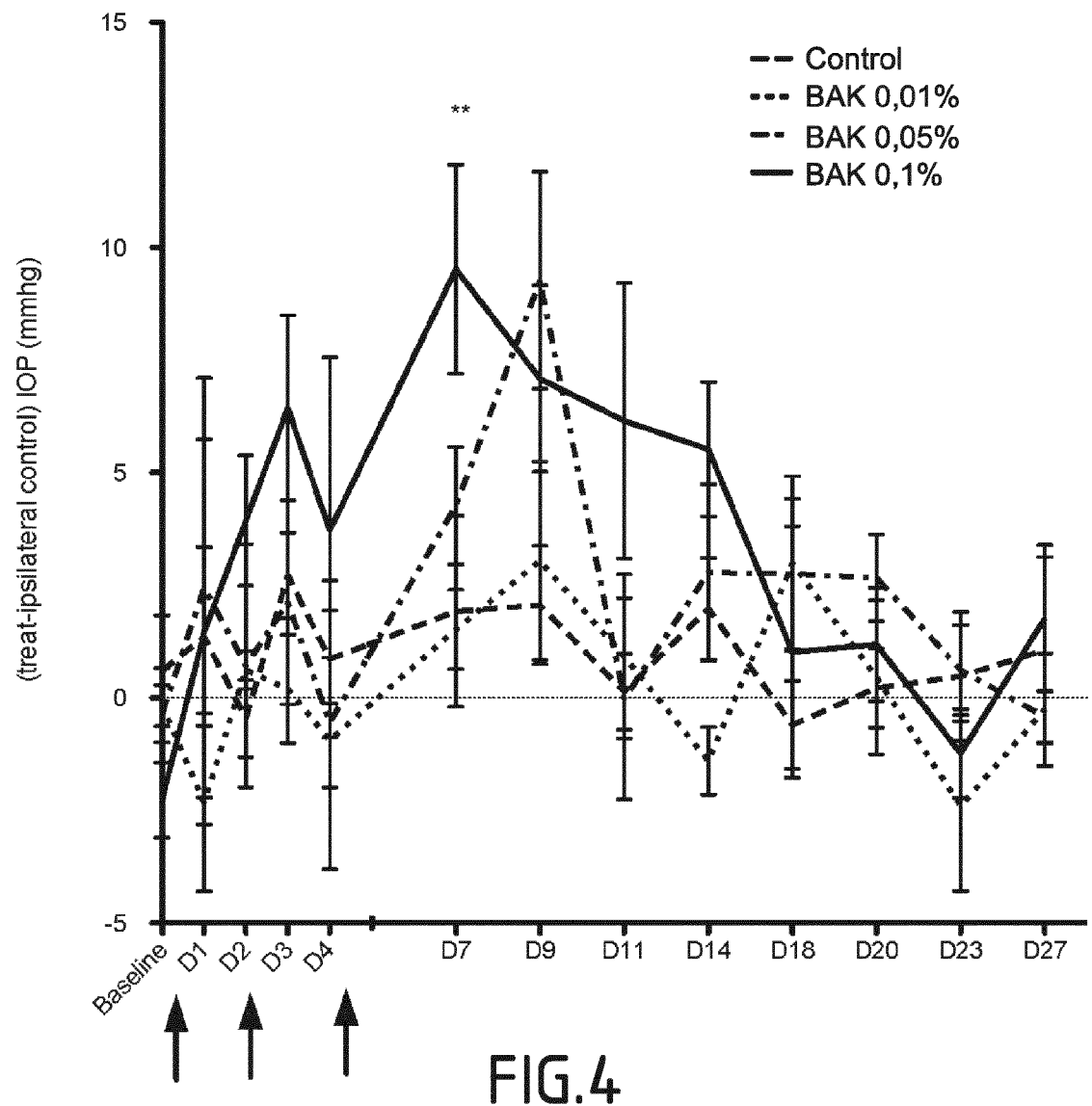
FIG. 4 shows the follow-up of intraocular pressure expressed as the difference between treated eye (right eye) and left control eye, following subconjunctival injection with different BAK concentrations or with a vehicle (control). Significant difference was found at D7, D11, and D14 for eyes injected with 0.1% BAK, and at D9 for eyes injected with 0.05% BAK.

BAK Subconjunctival Injections Induce Ocular Hypertension in a Dose-Dependent Manner 0.1% BAK injections induced a significant increase in intraocular pressure at D7, D11 and D14 with maximal effect occurring at D7 (see FIG. 4). 0.05% BAK injections induced a significant ocular hypertension at D9. Other times or BAK concentrations did not show significant changes in intraocular pressure.

BAK Subconjuctival Injections Do Not Lead to Significant Ocular Surface Damage

Figure 5:
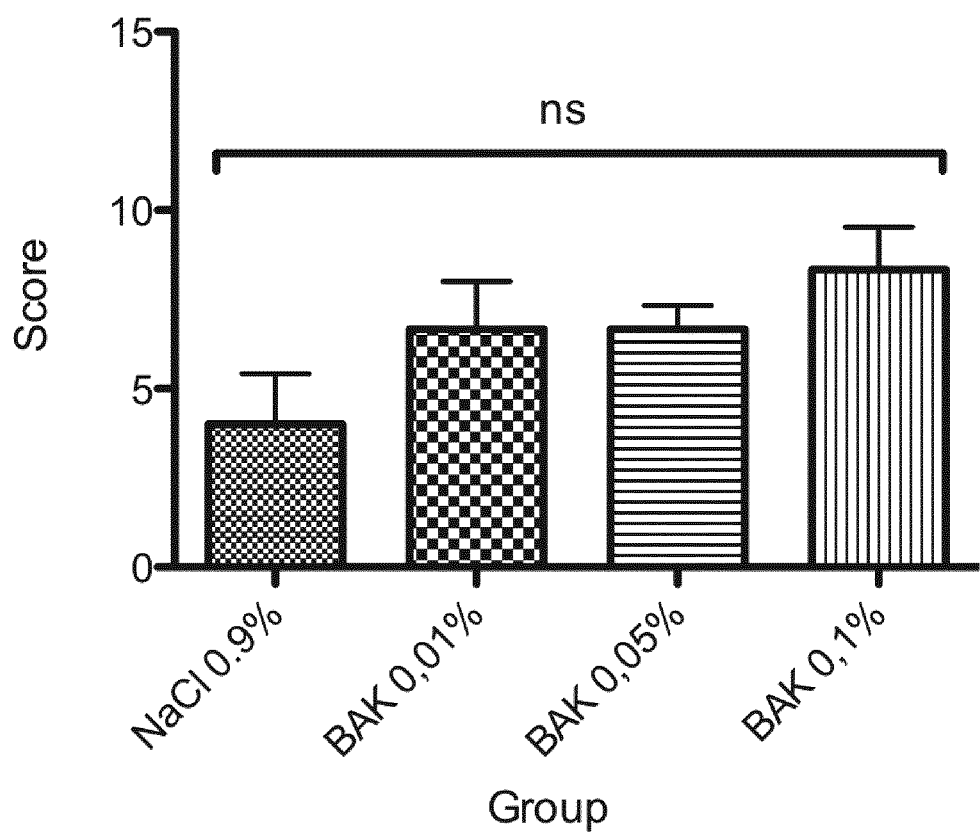
FIG. 5 shows the mean in vivo confocal microscopy score, as an evaluation of the ocular surface toxicity of subconjunctival injections with different BAK concentrations or with a control (NaCl), 30 days after the first BAK administration. No significant difference was found between the 4 independent samples (ns, p>0.05).

IVCM scores were used to evaluate ocular surface toxicity profiles in the 4 groups (vehicle, 0.01% BAK, 0.05% BAK, and 0.1% BAK) in different histological regions (superficial epithelium, basal epithelium, anterior stroma, limb and conjunctival stroma), 30 days after the first BAK administration (see Table 1). No statistical difference was found in the overall score between each groups (Kruskal Wallis test, p>0.05) (see FIG. 5).

TABLE 1

In vivo confocal microscopy scoring for the evaluation of ocular toxicity in the cornea, limbus and conjunctiva (maximum score 36 points)

| Eye zone | Toxicity seen | IVCM score |
|---|---|---|
| Superficial epithelium (Max 10) | Desquamation | 0-2 |
| | Shape/size: anisocytosis, macrocytosis, oedematous cells, swollen cells | 0-4 |
| | Reflectivity: abnormal reflectivity patterns | 0-4 |
| Basal epithelium (Max 6) | Disorganisation | 0-2 |
| | Inflammatory infiltration | 0-4 |
| Anterior stroma (Max 10) | Disorganisation | 0-2 |
| | Inflammatory infiltration | 0-2 |
| | Subasal nerve plexi hyperplasia | 0-2 |
| | Neovascularisation | 0-4 |
| Limbus and conjunctiva (Max 10) | Presence of abnormal capillary bud from limbal vessels | 0-4 |
| | Presence of hyperdilated vessels (>75 micrometers) | 0-4 |
| | Presence of inflammatory infiltrates, rolling in limbal vessels/conjunctival zone | 0-2 |

The following BAK-induced ocular surface changes were observed using in vivo confocal microscopy (IVCM subscores):

Superficial epithelium: slight epithelial swelling was found in all the animals;

Basal epithelium: basal epithelium was unchanged and there were no significant differences between the 4 groups;

Anterior stroma: there was a trend for hyperplasia of the subbasal nerve plexi in the BAK 0.1% group;

Limbus and conjunctiva: peripheral vasodilatation was found in one 0.01% BAK, and in three 0.1% BAK;

Posterior stroma and endothelium: no toxicity was found in the posterior stroma or endothelium.

Neither anterior eye abnormality nor ocular surface pathological changes were found whatever the BAK concentration.

The invention claimed is:

1. A method for inducing an increase in intraocular pressure in an animal, said method comprising a step of ocularly administering a solution comprising benzalkonium chloride (BAK) to said animal, wherein the step of ocularly administering is done by injection and wherein the solution comprises a concentration of BAK greater than 0.03%, wherein the increase in the intraocular pressure is sufficient to serve as a model of glaucoma.

2. The method of claim 1, wherein the solution comprises a concentration of BAK between 0.05% and 0.5%.

3. The method of claim 1, wherein the injection is performed in the subconjunctival region.

4. The method of claim 1, wherein said method comprises multiple steps of ocularly administering the solution comprising BAK.

* * * * *